United States Patent
Masini (10) Patent No.: US 6,398,812 B1
(45) Date of Patent: Jun. 4, 2002

(54) SHOULDER PROSTHESIS WITH ANATOMIC REATTACHMENT FEATURES

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 0 days.

(21) Appl. No.: 09/500,827

(22) Filed: Feb. 10, 2000

(51) Int. Cl.[7] ................................................. A61F 2/40
(52) U.S. Cl. .................................. 623/19.14; 623/19.11
(58) Field of Search ............................. 623/19.14, 23, 623/19

(56) References Cited

U.S. PATENT DOCUMENTS

| | | | |
|---|---|---|---|
| 4,045,825 A | 9/1977 | Stroot | 3/1.91 |
| 4,355,427 A | * 10/1982 | Schneider | 3/1.91 |
| 5,282,865 A | 2/1994 | Dong | 623/19 |
| 5,702,486 A | * 12/1997 | Craig et al. | 623/23 |
| 5,944,758 A | * 8/1999 | Mansat et al. | 623/19 |
| 5,961,555 A | * 10/1999 | Huebner | 623/19 |

OTHER PUBLICATIONS

Richards Manufacturing Co. "H–J–B Shoulder Prosthesis", Journal of Bone & Joint Surgery, Mar. 1964, p. 17.

* cited by examiner

*Primary Examiner*—Corrine McDermott
*Assistant Examiner*—Thomas Barrett
(74) *Attorney, Agent, or Firm*—Gifford, Krass, Groh, Sprinkle, Anderson & Citkowski, PC (57) ABSTRACT

A humeral prosthesis features improved anatomic attachment areas for tendon or bone. In the preferred embodiment, in contrast to existing devices, at least one set of tendon/bone attachment points are provided along a line, at least a portion of which is divergent with respect to the axis of the stem. One or more sets of attachment points may be further be provided along a line which is substantially parallel to the axis of the stem, resulting in a "T" "L" or "U" shape. Alternatively, attachment points having a changing degree of diversion with respect to the axis of the stem may be provided along a common, curved line. The attachment points may simply be apertures formed through the body of the implant though, in the preferred embodiment, the apertures are provided on raised tabs. An area of bone-ingrowth material may be provided adjacent the attachment points, and may include a separate fastening mechanism such as a threaded hole to receive a screw. A groove may also be provided in any embodiment to receive the biceps tendon. Particularly with respect to fractures, including multi- and 'four-part' fractures, means specifically intended for the rigid reattachment of the greater or lesser tuberosities may be provided separately or in conjunction with other sets of reattachment configurations.

60 Claims, 7 Drawing Sheets

Fig - 1A
*(PRIOR ART - USP #5,282,865)*

SHOULDER PROSTHESIS WITH ANATOMIC REATTACHMENT FEATURES

FIELD OF THE INVENTION

This invention relates generally to orthopedic surgery and, in particular, to improved shoulder prostheses featuring more anatomic rotator cuff attachment geometries facilitating enhanced fixation of tendon and/or bone.

BACKGROUND OF THE INVENTION

Figure 1A:
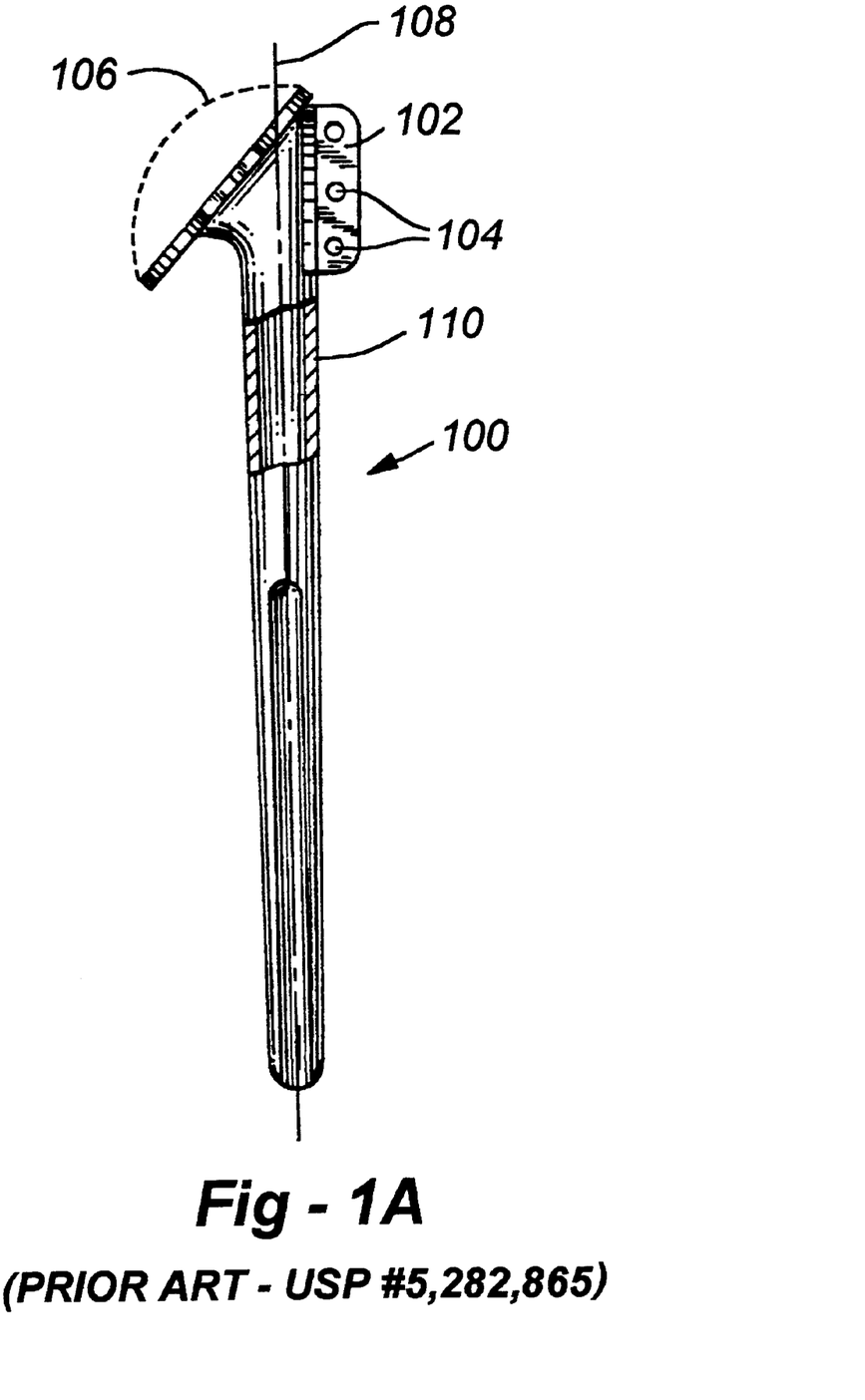
FIG. 1A is a drawing of a prior-art humeral prosthesis.

A typical proximal humeral prosthesis is depicted generally at 100 in FIG. 1, this particular drawing being taken in part from U.S. Pat. No. 5,282,865. The device includes a modular head attachment 106, though variations of such devices exist, including those without modularity, and designs incorporating different modular arrangements.

A tab 102 is provided on the lateral side of the prosthesis, as shown. The tab 104 is provided with two or more holes 106 disposed parallel to the length of the prosthesis; that is, parallel to the axis 108 of the stem 110. Although the stated purpose of the apertured tab 102 is to assist with installation of the device and to minimize rotation once installed, it is common practice in repairing a fracture to bring previously detached tendons together and suture them to this vertical tab on the lateral side of the prosthesis.

The tendons which are detached during the procedure may include the subscapularis tendon, the supraspinatus tendon, the infraspinatus tendon, and the teres minor tendon, the anatomy of each being well known, particularly to orthopedic surgeons. Since, in the case of a natural humerus, these tendons attach at different points of the bone to perform specific functions, vertically oriented tabs such as tab 102 in FIG. 1 does not adequately accommodate human anatomy.

More particularly, existing configurations are acceptable only with respect to the attachment of the posterior and anterior tendons. Since the supraspinatus tendon naturally lies flat along the top surface of the bone, the use of a vertical tab leads to an orientation which is perpendicular to the desired attachment configuration. This result, being anatomically incorrect, typically results in a reduced range of motion and strength following the procedure, particularly in initiating abduction; that is, in raising that arm. This is especially true in proximal humerus fractures known as 'four-part' fractures involving the head, shaft, greater tuberosity, and lesser tuberosity. Re-attachment to a vertical fin with sutures results in poor fixation in a non-anatomic arrangement.

SUMMARY OF THE INVENTION

The subject invention resides in a humeral prosthesis with improved anatomic attachment areas for tendon or bone. As in prior-art devices, the invention includes an elongated body having a proximal end and a distal end terminating in a stem with an axis configured for placement within an intramedullary canal of a humerus. In the preferred embodiment of the invention, however, and in contrast to existing devices, at least one set of tendon/bone attachment points are provided along a line, at least a portion of which is divergent with respect to the axis of the stem.

One or more sets of attachment points may further be provided along a line which is substantially parallel to the axis of the stem, resulting in a "T," "U" or "L" configuration, including inverted versions thereof. Alternatively, attachment points having a changing degree of diversion with respect to the axis of the stem may be provided along a common, curved line. The attachment points may simply be apertures formed through the body of the implant though, in the preferred embodiment, the apertures are provided on raised tabs. An area of bone-ingrowth material may be provided adjacent to or at the attachment site, and may include a separate fastening mechanism such as a threaded hole to receive a screw, or any other alternative means operative to rigidly attach the tendon or bone to the prosthesis. A groove may also be provided in any embodiment to receive the biceps tendon. In addition, a recess may be provided to accept a tendon-bone unit such as the greater or lesser tuberosities with their respective tendons attached. Particularly with respect to fractures, including multi- and 'four-part' fractures, means specifically intended for the rigid reattachment of the greater or lesser tuberosities may be provided separately or in conjunction with other sets of reattachment configurations.

DETAILED DESCRIPTION OF THE INVENTION

As discussed above, this invention is directed to humeral prostheses providing more anatomical attachment configurations for bone and/or tendons, with the goal being a greater range of post-operative motion and/or strength. Before discussing the various embodiments of the invention in detail, it will be helpful to introduce aspects of the anatomy associated with procedures contemplated herein.

Figure 1B:
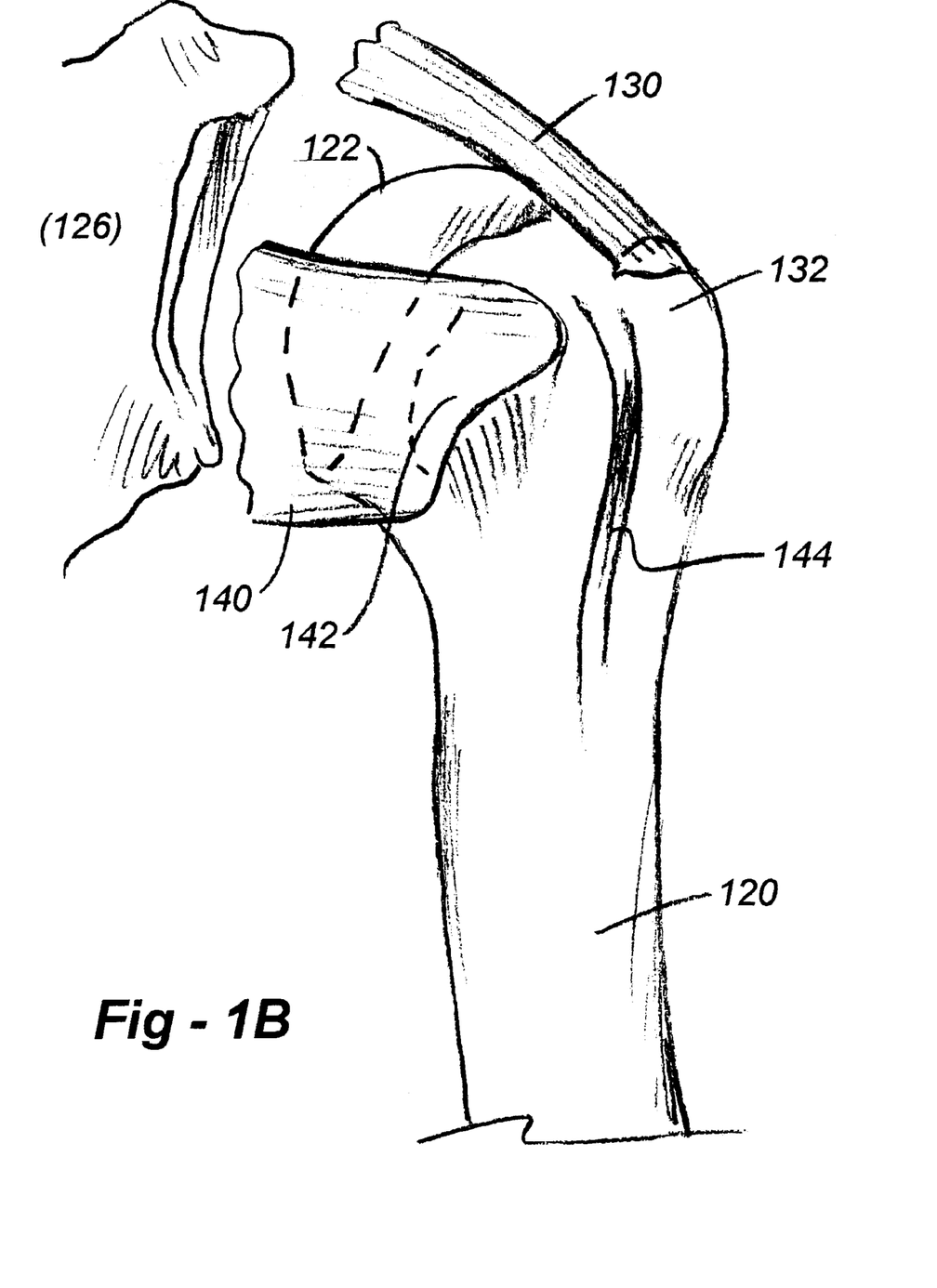
FIG. 1B is a drawing of proximal humerus and anatomic tendon attachments.

Fig. 1B is a drawing of a human proximal humerus showing the natural anatomic tendon attachment areas. The humerus, 120, includes a proximal portion having a head 122 with an articulating surface adapted to co-act with the glenoid bone 126 in the shoulder joint. The supraspinatus tendon 130 lies flat on the proximal humerus, and attaches at a section of bone called the greater tuberosity 132. The subscapularis tendon 140 extends across the side of the joint and attaches at the lesser tuberosity 142. A groove 144 receives the biceps tendon (not shown).

Figure 1C:
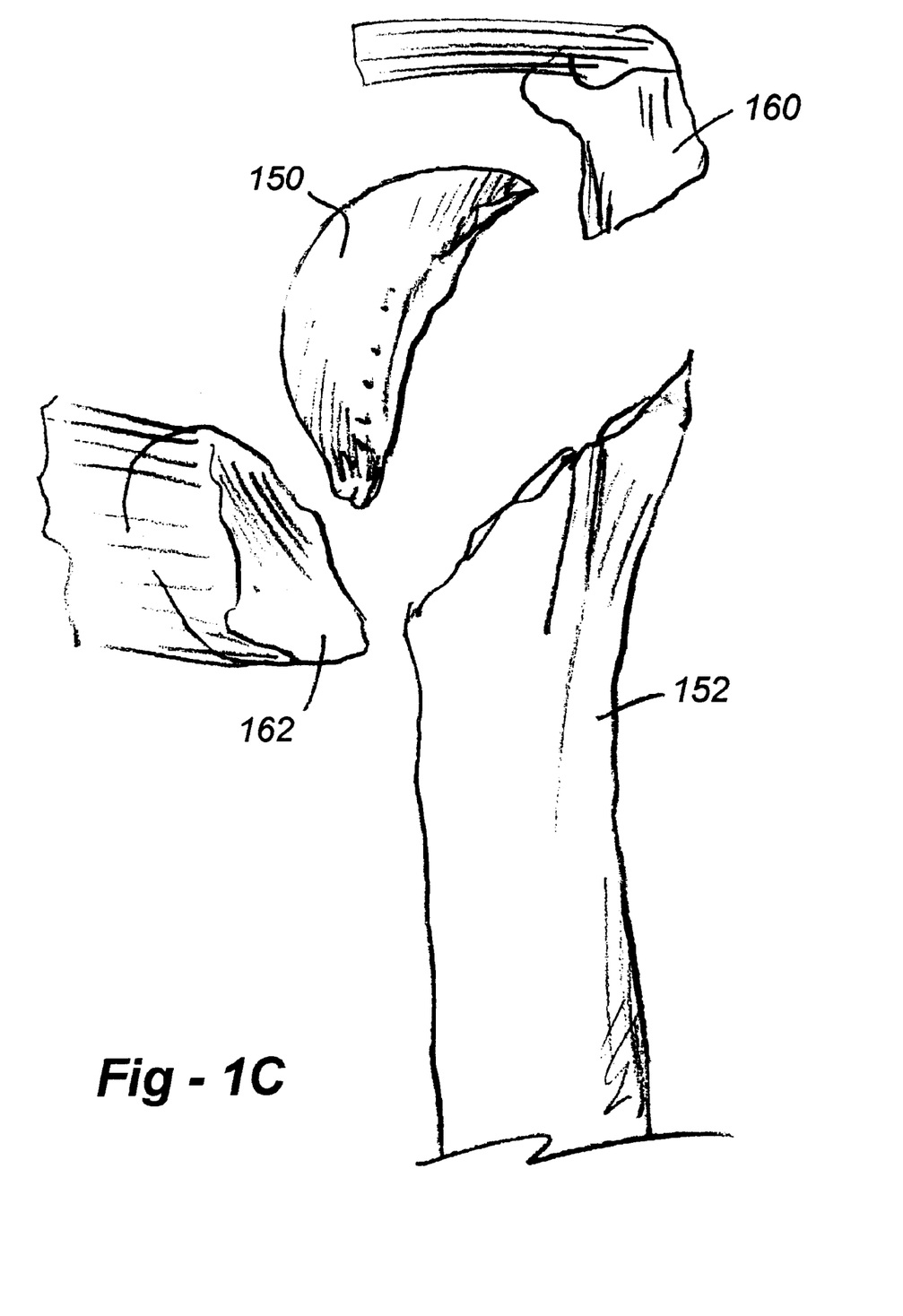
FIG. 1C is a drawing of a four-part fracture to which the subject invention is applicable.

FIG. 1C is a drawing which illustrates what typically occurs during a multi-part fracture of the proximal humerus, in the case a so-called four-part fracture to which the subject invention is applicable. In particular, the bone shatters, leaving a separate head and shaft portion 150 and 152. In addition, the greater tuberosity 160 breaks off with the supraspinatus tendon attached thereto. The lesser tuberosity 162 also forms a separate piece with the subscapularis tendon attached to that piece, as shown. The infraspinatus and teres minor tendons may be attached to the greater tuberosity as well or to separate fragments.

Figure 2A:
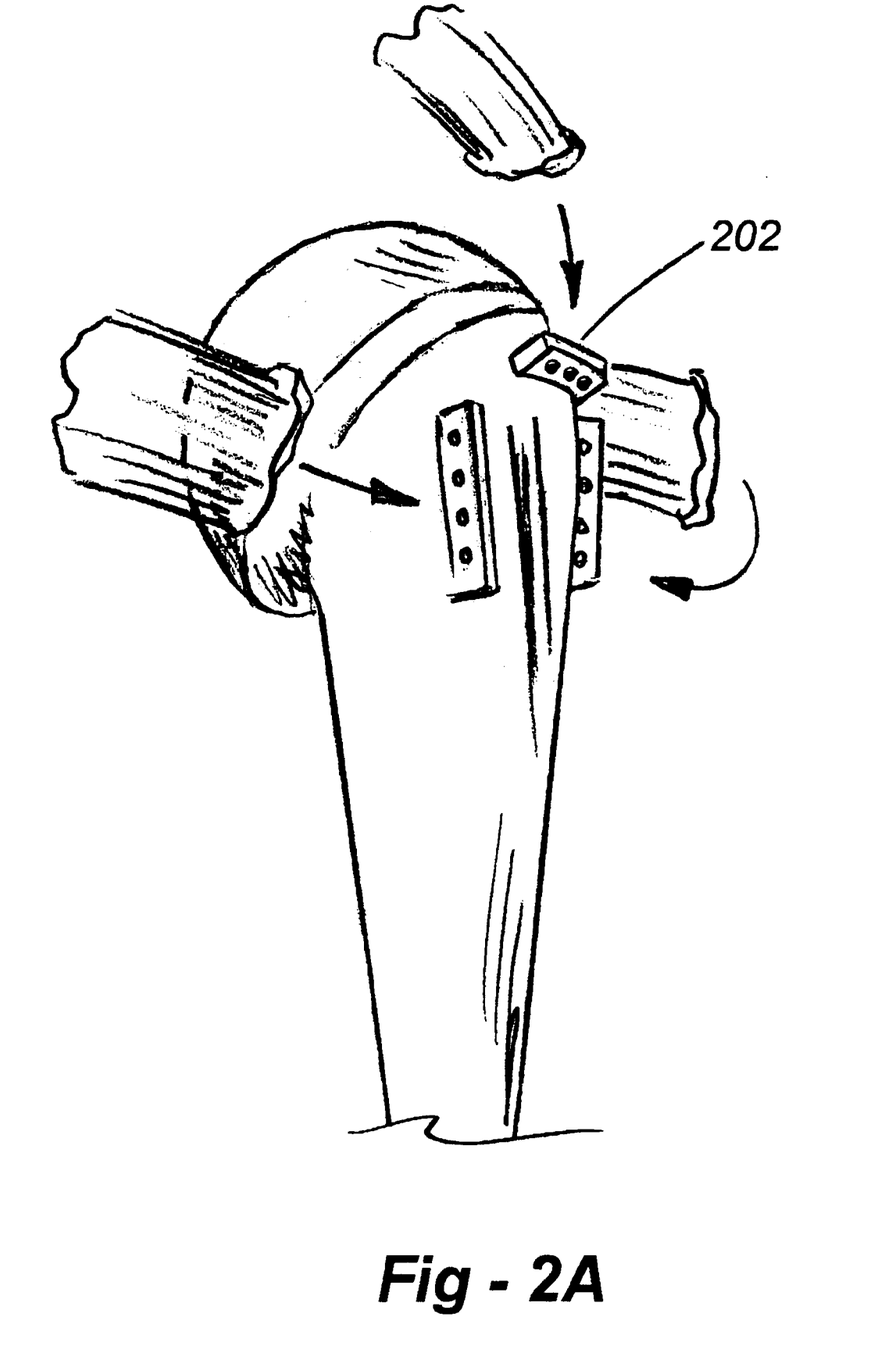
FIG. 2A is a lateral view of a humeral prosthesis according to the invention having an inverted-U bone/tendon attachment configuration.

Reference is now made to FIG. 2A, which is a lateral view of a humeral prosthesis according to the invention. Broadly, an anterior—to—posterior feature such as tab 202 is provided for attachment of the supraspinatus. Although tab 202 is shown generally transverse to the axis of the implant, the invention anticipates other orientations, described herein, with the basic premise being that one or more sets of divergent attachment points are provided for a more anatomical compliance with the rotator cuff. By 'divergent,' it is meant that the set of connection points tend away from a line strictly parallel to the axis of the implant which, of course, would include one or more connectors which are transverse or perpendicular to the axis of the implant, regardless of the muscular attachments.

Figure 2B:
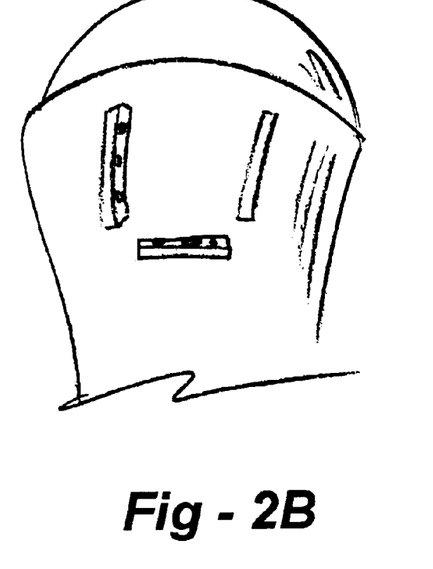
FIG. 2B is a lateral view of a humeral prosthesis according to the invention having a non-inverted-U bone/tendon attachment configuration.
Figure 2C:
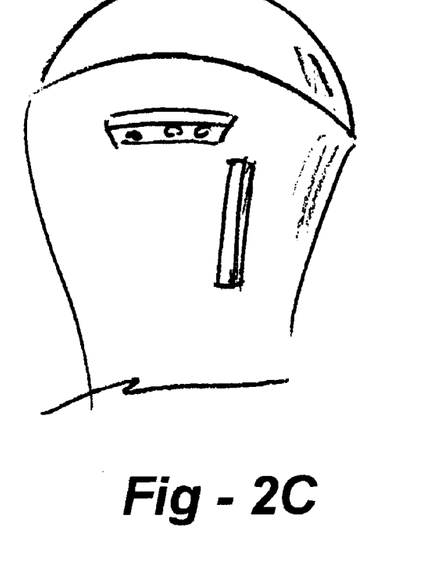
FIG. 2C is a lateral view of a humeral prosthesis according to the invention having an inverted L-shaped bone/tendon attachment configuration.
Figure 2D:
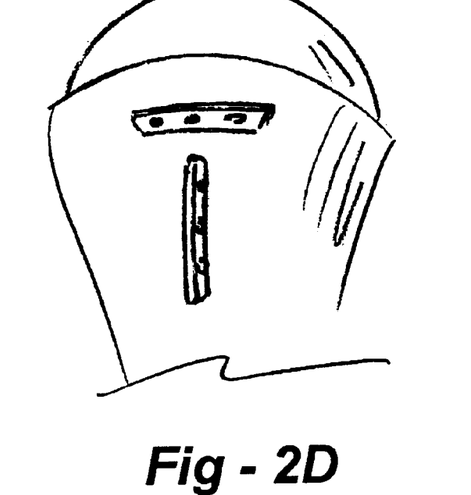
FIG. 2D is a lateral view of a humeral prosthesis according to the invention having a T-shaped bone/tendon attachment configuration.

Having provided this facility, other tabs or attachment mechanisms be added for the anterior and/or posterior tendons, resulting in the preferred inverted "U" shape of FIG. 2A. An inverted-U is not the only tab configuration providing a more anatomic bone/tendon attachment arrangement according to the invention. As shown in FIG. 2B, a non-inverted-U bone/tendon attachment configuration may alternatively be provided, or an inverted L-shaped bone/tendon attachment configuration (FIG. 2C). As a further alternative, both anterior and posterior tendons may be attached to a single substantially vertical feature, with the result being a "T" shape, as shown in FIG. 2D. Other geometries are also possible, including non-inverted and rotated L and T shapes, as long as separate and distinct regions are provided for reattachment of the greater and lesser tuberosities.

Figure 3:
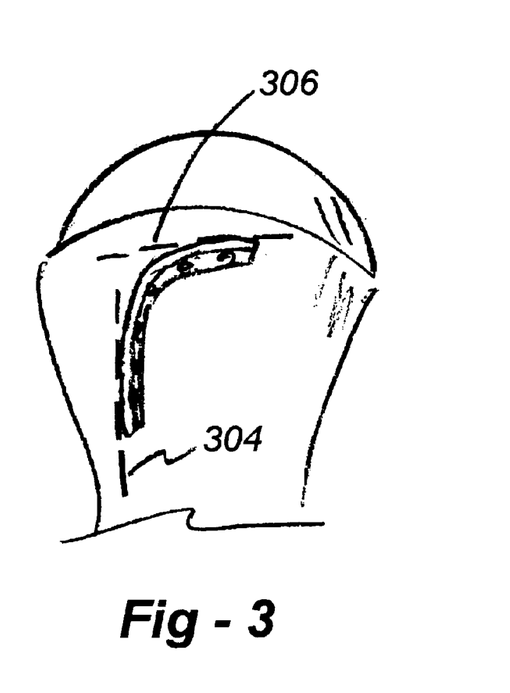
FIG. 3 is an alternative embodiment of the invention, wherein a plurality of attachment points are arranged along a common curved line.
Figure 4:
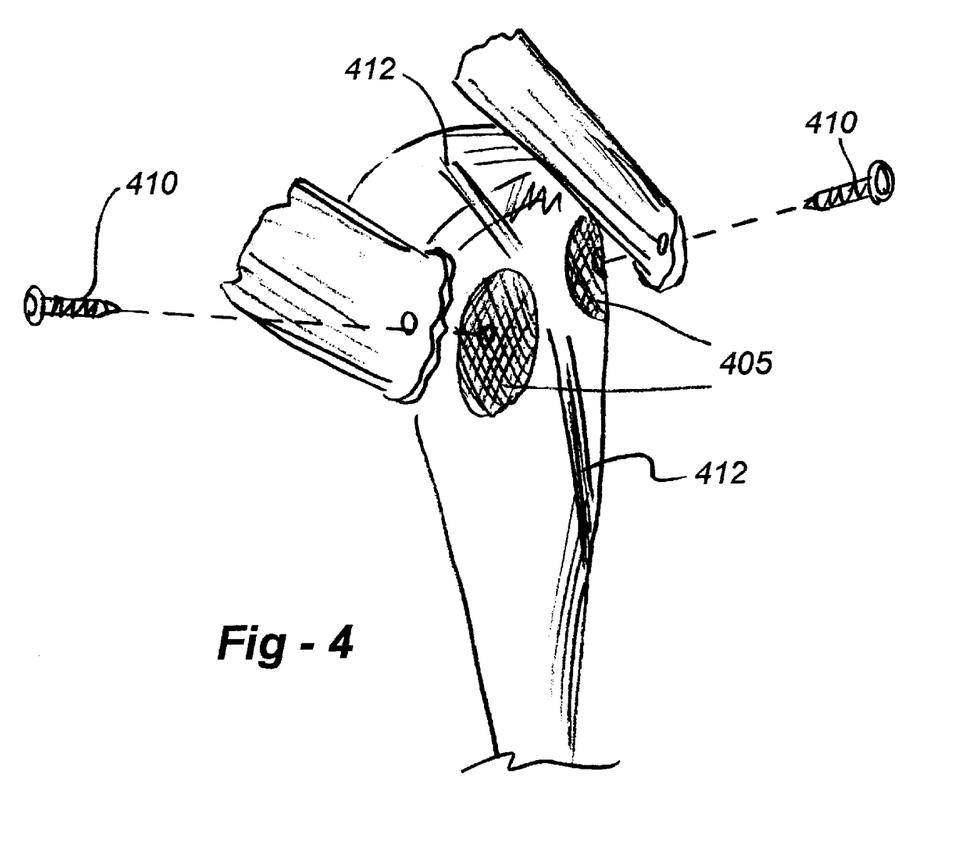
FIG. 4 illustrates how bone-ingrowth sections are provided as localized sites along with fastening means to hold bone/tendon pieces in place.

Note also that separate tab segments need not be used, in that one or more curved features may be provided, preferably with tangents 304 and 306 substantially along the axis of the implant and transverse thereto, as shown in FIG. 3. To enhance reattachment, one or more of the tabs or other features may be coated with a bone-ingrowth material or bone-ongrowth material. Biologic enhancements such as hydroxyapatite may also be provided. As a further alternative, as shown in FIG. 4, bone-ingrowth sections may be provided as localized areas 405, along with fasteners such as screws 410 to hold the bone/tendon pieces in place. In this and each of the embodiments described herein, a groove 412 may be provided in the head and/or side portions of the prosthesis to receive the biceps tendon.

Figure 5:
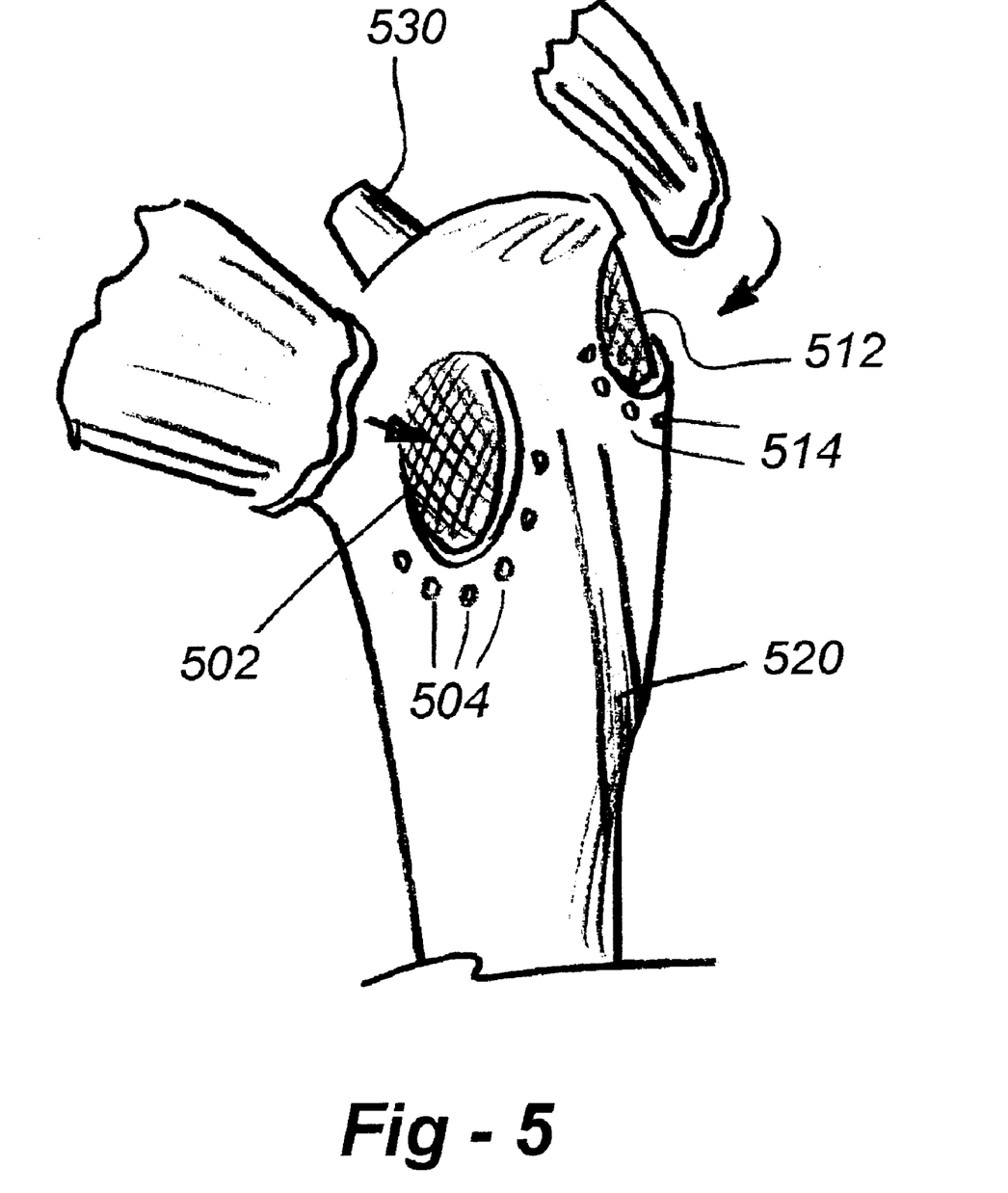
FIG. 5 is a drawing which shows a bone-ingrowth areas provided for greater and lesser tuberosities in conjunction with separate sets of suture points.

The areas of bone-ingrowth material may be provided along with, or apart from, the tabs or other reattachment facilities discussed elsewhere herein. For example, as shown in FIG. 5, a bone-ingrowth area 502 for lesser tuberosity may be provided in conjunction with suture holes 504, and/or ingrowth area 512 may be provided for greater tuberosity in conjunction with suture holes 514. Note that the suture holes need not be provided on a raised tab, but may be located along a ridge or depression, as convenient to the embodiment. In all embodiments, the invention is compatible with modular head/neck attachments as discussed in the Background of the Invention. FIG. 5, for example, shows a post 530 associated with a modular head attachment. The groove 520 is optionally be provided to receive the biceps tendon, as discussed above.

I claim:

1. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity;

a set of suture holes located distally of the region; and a set of tendon or bone reattachment points arranged along a line which is substantially parallel to the axis of the stem, thereby forming a "T" shape with the set of suture holes.

2. The prosthesis of claim 1, wherein at least some of the suture holes are disposed on a raised tab.

3. The prosthesis of claim 1 wherein the region includes an area of bone-ingrowth, ongrowth or biologic enhancement material.

4. A prosthesis applicable to fractures of the humerus, including multi-part fractures wherein the greater or lesser tuberosities require reattachment, the prosthesis comprising:

an elongated body having a proximal end and a distal end terminating in a stem configured for placement within an intramedullary canal of a humerus, such that a portion of the proximal end remains exposed following installation;

at least one area on the exposed portion of the proximal end, the location of the area being physically configured for reattachment of one of the greater or lesser tuberosities; and a rigid fastener for reattaching one of the tuberosities to the area.

5. The prosthesis of claim 4, wherein:

the rigid fastener is a threaded fastener.

6. The prosthesis of claim 4, wherein:

the area further includes a bone-ingrowth, ongrowth, or biologic enhancement surface.

7. The prosthesis of claim 4, wherein:

the area on the exposed portion is recessed.

8. The prosthesis of claim 4, wherein two separate distinct regions are provided for reattachment of the greater and lesser tuberosities, respectively.

9. The prosthesis of claim 8, wherein each of the distinct regions includes a bone ingrowth, ongrowth, or biologic enhancement surface.

10. The prosthesis of claim 9, wherein the bone ingrowth or ongrowth surfaces include a biologic enhancement material.

11. The prosthesis of claim 8, wherein each region is recessed.

12. The prosthesis of claim 8, further including a fastener for rigidity attaching each fragment to its respective region.

13. The prosthesis of claim 12, including threaded fasteners.

14. A prosthesis applicable to fractures of the humerus, including multi-part fractures wherein fragments of the greater and lesser tuberosities require reattachment, the prosthesis comprising:

an elongated body having a proximal end and a distal end terminating in a stem configured for placement within an intramedullary canal of a humerus, such that a portion of the proximal end remains exposed following installation;

two distinct and separate areas on the exposed portion of the proximal end, including a lateral area configured for reattachment of the greater tuberosity fragment and an anterior area configured for reattachment of the lesser tuberosity fragment; and a set of suture holes located distally with respect to the lateral area configured for the reattachment of the greater tuberosity fragment.

15. The prosthesis of claim 14, further including a fastener associated with each area enabling the respective fragments to be rigidly attached thereto.

16. A prosthesis applicable to fractures of the humerus, including multi-part fractures wherein a tuberosity requires reattachment, the tuberosity having an anatomical connection to a supraspinatus tendon defining a line of action, the prosthesis comprising:

an elongated body having a proximal end and a distal end terminating in a stem defining an axis, the stem being configured for placement within an intramedullary canal of a humerus such that a portion of the proximal end remains exposed;

a region on the exposed portion of the proximal end of the body physically configured to receive the tuberosity; and a set of suture holes arranged along a line which is substantially transverse to the line of action of the supraspinatus tendon.

17. The prosthesis of claim 16, further including an additional set of tendon or bone reattachment points arranged along a line which is substantially parallel to the axis of the stem.

18. The prosthesis of claim 16, wherein the set of suture holes and the additional tendon or bone reattachment points form a "T" shape.

19. The prosthesis of claim 16, wherein the set of suture holes and the additional tendon or bone reattachment points form an upright or inverted, forward or backward "L" shape.

20. The prosthesis of claim 16, wherein the set of suture holes and the additional tendon or bone reattachment points both lie along the same curved line.

21. The prosthesis of claim 16, further including two additional sets of tendon or bone reattachment points, each arranged along a separate line which is substantially parallel to the axis of the stem.

22. The prosthesis of claim 16, wherein the set of suture holes and the two additional sets of reattachment points form an upright or inverted "U" shape.

23. The prosthesis of claim 16, wherein the set of suture holes and the two additional sets of reattachment points all lie along the same curved line.

24. The prosthesis of claim 16, where at least some of the suture holes are disposed on a raised tab.

25. The prosthesis of claim 16, wherein the recessed region includes an area of bone-ingrowth, ongrowth or biologic enhancement material.

26. The prosthesis of claim 16, further including a groove to receive a biceps tendon.

27. The prosthesis of claim 16, wherein the suture holes are arranged along a line which is substantially perpendicular to the axis of the stem.

28. The prosthesis of claim 16, further including a rigid fastener to reattach the fragment to the region.

29. The prosthesis of claim 16, wherein:

the rigid fastener is threaded.

30. The prosthesis of claim 31, wherein:

the region includes a bone-ingrowth, ongrowth or biologic enhancement surface.

31. The prosthesis of claim 31, wherein:

the region is recessed.

32. A prosthesis applicable to fractures of the humerus, including multi-part fractures wherein a tuberosity requires reattachment, the tuberosity having an anatomical connection to a tendon defining a line of action, the prosthesis comprising:

an elongated body having a proximal end and a distal end terminating in a stem defining an axis, the stem being configured for placement within an intramedullary canal of a humerus such that a portion of the proximal end remains exposed; and two recessed regions on the exposed body, one configured to receive the greater tuberosity, and one configured to receive the lesser tuberosity.

33. The prosthesis of claim 32, further including a set of suture holes located distally with respect to each recessed region.

34. The prosthesis of claim 32 further including a set of suture holes arranged along a line which is substantially transverse to the line of action of the tendon.

35. The prosthesis of claim 34, where at least some of the suture holes are disposed on a raised tab.

36. The prosthesis of claim 34, where at least some of the tendon or bone reattachment points are disposed on a raised tab.

37. The prosthesis of claim 32, further including an additional set of tendon or bone reattachment points arranged along a line which is substantially parallel to the axis of the stem.

38. The prosthesis of claim 32, wherein each recessed region includes an area of bone-ingrowth, ongrowth or biologic enhancement material.

39. The prosthesis of claim 32, further including a groove to receive a biceps tendon.

40. The prosthesis of claim 39, further including a rigid fastener to reattach the fragment to the recessed region.

41. The prosthesis of claim 40, wherein the rigid fastener is threaded.

42. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity;

a set of suture holes located distally of the region; and a set of tendon or bone reattachment points arranged along a line which is substantially parallel to the axis of the stem, thereby forming an upright or inverted, forward or backward "L" shape with the set of suture holes.

43. The prosthesis of claim 42, wherein at least some of the suture holes are disposed on a raised tab.

44. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity;

a set of suture holes located distally of the region; and a set of tendon or bone reattachment points arranged such that the set of suture holes and the additional tendon or bone reattachment points lie along the same curved line.

45. The prosthesis of claim 44, wherein at least some of the suture holes are disposed on a raised tab.

46. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity;

a set of suture holes located distally of the region; and two additional sets of tendon or bone reattachment points, each arranged along a separate line which is substantially parallel to the axis of the stem.

47. The prosthesis of claim 46, wherein the set of suture holes and the two additional sets of reattachment points form an upright or inverted "U" shape.

48. The prosthesis of claim 46, wherein the set of suture holes and the two additional sets of reattachment points all lie along the same curved line.

49. The prosthesis of claim 46, where at least some of the suture holes are disposed on a raised tab.

50. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity;

a set of suture holes located distally of the region; and a groove on the exposed portion to receive a biceps tendon.

51. The prosthesis of claim 50, wherein the region includes an area of bone-ingrowth, ongrowth or biologic enhancement material.

52. A humeral prosthesis with anatomic reattachment features, comprising:

an elongated body having a proximal end and a distal end terminating in a stem with an axis, the stem being configured for placement within an intramedullary canal of a humerus such that a portion of the proximal end remains exposed;

a region on the exposed portion of the proximal end of the body configured to receive a fragment of a greater or lesser tuberosity; and a set of suture holes located distally of the region along a line which is substantially perpendicular to the axis of the stem.

53. A humeral prosthesis with anatomic reattachment features, comprising:

an elongated body having a proximal end and a distal end terminating in a stem with- an axis, the stem being configured for placement within an intramedullary canal of a humerus such that a portion of the proximal end remains exposed;

a region on the exposed portion of the proximal end of the body configured to receive a fragment of a greater or lesser tuberosity, including a set of suture holes located distally of the region; and a rigid fastener to reattach the fragment to the region.

54. The prosthesis of claim 53, wherein the rigid fastener is threaded.

55. The prosthesis of claim 53; wherein the region includes a bone-ingrowth, ongrowth or biologic enhancement surface.

56. The prosthesis of claim 53, wherein the region is recessed.

57. A prosthesis applicable to fractures of the humerus, including multi-part fractures wherein fragments of the greater and lesser tuberosities require reattachment, the prosthesis comprising:

an elongated body having a proximal end and a distal end terminating in a stem configured for placement within an intramedullary canal of a humerus, such that a portion of the proximal end remains exposed following installation;

two distinct and separate areas on the exposed portion of the proximal end, including a lateral area configured for reattachment of the greater tuberosity fragment and an anterior area configured for reattachment of the lesser tuberosity fragment; and wherein each area includes a region of bone ingrowth, ongrowth, or biologic enhancement material.

58. A prosthesis applicable to fractures of the humerus, including multi-part fractures wherein a tuberosity requires reattachment, the tuberosity having an anatomical connection to a tendon defining a line of action, the prosthesis comprising:

an elongated body having a proximal end and a distal end terminating in a stem defining an axis, the stem being configured for placement within an intramedullary canal of a humerus such that a portion of the proximal end remains exposed;

a recessed region on the exposed portion of the proximal end of the body physically configured to receive the tuberosity; and a set of suture holes arranged along a line which is substantially transverse to the line of action of the tendon.

59. A prosthesis applicable to fractures of the humerus, including multi-part fractures wherein a tuberosity requires reattachment, the tuberosity having an anatomical connection to a tendon defining a line of action, the prosthesis comprising:

an elongated body having a proximal end and a distal end terminating in a stem defining an axis, the stem being configured for placement within an intramedullary canal of a humerus such that a portion of the proximal end remains exposed;

a region on the exposed portion of the proximal end of the body physically configured to receive the tuberosity, including a set of suture holes arranged along a line which is substantially transverse to the line of action of the tendon; and a rigid fastener for attaching the tuberosity to the region.

60. The prosthesis of claim 59, wherein the rigid fastener is threaded.

* * * * *